(12) United States Patent
Nakagawa et al.

(10) Patent No.: US 9,453,815 B2
(45) Date of Patent: Sep. 27, 2016

(54) GAS SENSOR

(75) Inventors: Masaki Nakagawa, Komaki (JP); Koji Shiotani, Kasugai (JP); Tomohiro Wakazono, Konan (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 668 days.

(21) Appl. No.: 13/554,340

(22) Filed: Jul. 20, 2012

(65) Prior Publication Data

US 2013/0019655 A1    Jan. 24, 2013

(30) Foreign Application Priority Data

Jul. 21, 2011   (JP) .................................. 2011-159950

(51) Int. Cl.
*G01N 27/419* (2006.01)

(52) U.S. Cl.
CPC .................................. *G01N 27/419* (2013.01)

(58) Field of Classification Search
CPC ............ G01N 27/404–27/407; G01N 27/409; G01N 27/416; G01N 27/419; G01N 27/41
See application file for complete search history.

(56) References Cited

U.S. PATENT DOCUMENTS

| | | | |
|---|---|---|---|
| 6,699,376 B2* | 3/2004 | Naito | 204/429 |
| 2010/0180665 A1* | 7/2010 | Abe et al. | 73/23.31 |
| 2010/0264027 A1 | 10/2010 | Nakagawa et al. | |
| 2011/0168574 A1* | 7/2011 | Sasaki | 205/775 |

FOREIGN PATENT DOCUMENTS

JP      2010-266429 A    11/2010

* cited by examiner

*Primary Examiner* — Jennifer Dieterle
(74) *Attorney, Agent, or Firm* — Sughrue Mion, PLLC (57) ABSTRACT

In a gas sensor element of a gas sensor, reference oxygen chamber (113) assumes the shape of a rectangular parallelepiped. A reference electrode (111) is disposed on a surface of a third solid electrolyte body (73) which is exposed to the reference oxygen chamber (113). A second outer electrode (117) is disposed opposite the reference electrode, on a surface of a second solid electrolyte body (77) which is exposed to the reference oxygen chamber. Further, a porous, insulative protection layer (165) is formed so as to cover the entire surface of the second outer electrode. A gap (167) is present between the reference electrode and the insulative protection layer. The thickness of the gap is greater than that of the insulative protection layer.

10 Claims, 9 Drawing Sheets

GAS SENSOR

BACKGROUND OF THE INVENTION

1. Field of the Invention

The present invention relates to a gas sensor for measuring a particular gas component of exhaust gas from, for example, an internal combustion engine of an automobile.

2. Description of the Related Art

Conventionally, gas sensors have been utilized for detecting particular gas components, such as nitrogen oxides (NOx) and oxygen, and for measuring the concentrations of particular gas components.

Among these gas sensors, a gas sensor is known that uses an elongated-plate-like gas sensor element configured such that a plurality of ceramic layers (e.g., solid electrolyte layers and alumina substrates) are laminated.

A known technique that utilizes through-holes extending through laminated ceramic layers is used for electrically connecting internal conductors (e.g., a heat-generating resistor and electrodes) of the gas sensor element to corresponding electrode pads provided on the surface of the gas sensor element.

For example, Patent Document 1 mentioned below discloses a plate-like gas sensor element in which a plurality of solid electrolyte substrates, etc., are laminated together.

Figure 9:
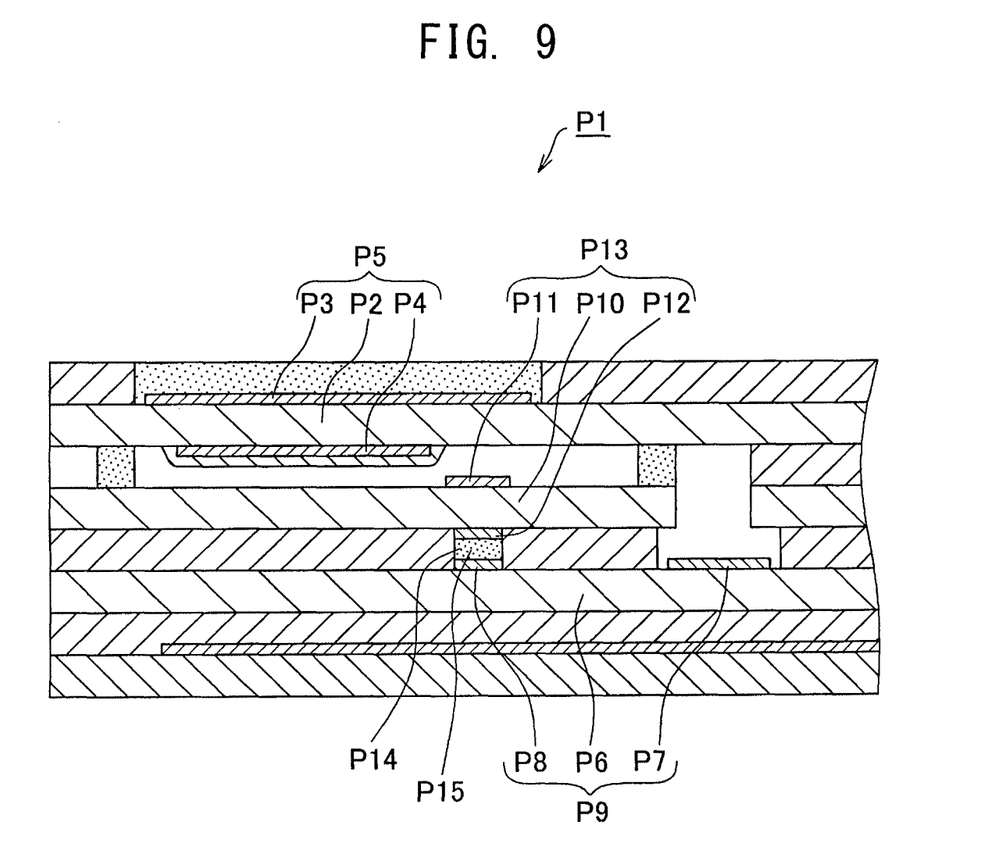
FIG. 9 is an explanatory view showing the inner structure of a conventional gas sensor element.

Specifically, a gas sensor having the above-mentioned gas sensor element is mounted to, for example, an exhaust pipe of an internal combustion engine of an automobile. As shown in FIG. 9, a gas sensor element P1 is a plate-like laminate of a first pump cell P5 in which a pair of first electrodes P3 and P4 is provided on a first solid electrolyte body P2, a second pump cell P9 in which a pair of second electrodes P7 and P8 is provided on a second solid electrolyte body P6, an oxygen concentration detection cell P13 in which a pair of third electrodes P11 and P12 is provided on a third solid electrolyte body P10, etc.

Furthermore, the gas sensor element P1 has a reference oxygen chamber P14 between the second solid electrolyte body P6 and the third solid electrolyte body P10. In the reference oxygen chamber P14, one electrode (second outer electrode) P8 of the two second electrodes and one electrode (reference electrode) P12 of the two third electrodes are disposed opposite each other. Furthermore, in order to prevent contact between the two electrodes P8 and P12, the reference oxygen chamber P14 has an insulative protection layer P15 formed from an electrically insulative porous material between the two electrodes P8 and P12.

Furthermore, the electrodes P3, P4, P7, P8, P11, P12 are electrically connected to corresponding electrode pads P22 (see FIG. 10) provided on the outer surface of a rear end portion of the gas sensor element P1, via leads and through-holes.

Figure 10:
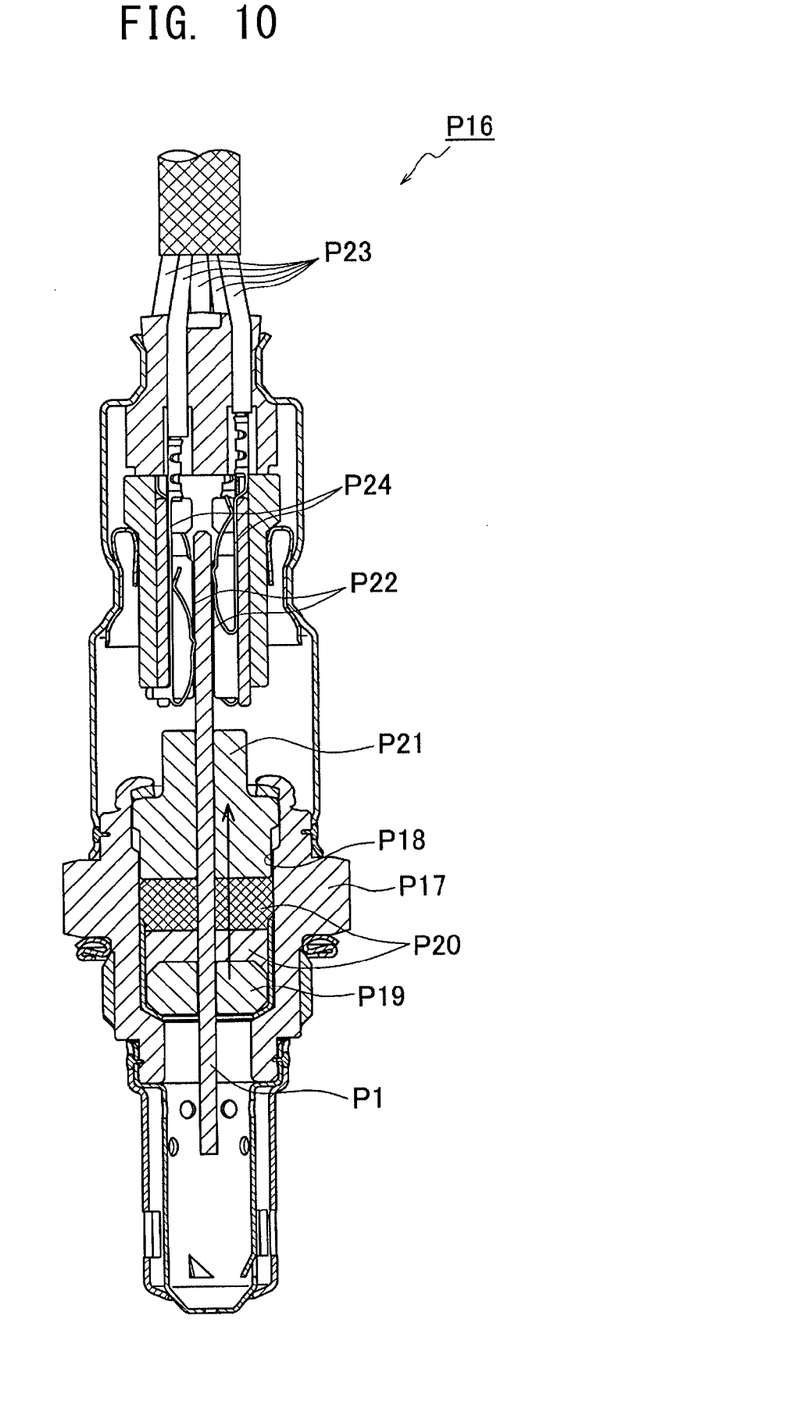
FIG. 10 Explanatory view showing a conventional NOx sensor.

As shown in FIG. 10, in a gas sensor P16, the gas sensor element P1 is disposed so as to extend through a ceramic holder P19, talc P20, and a ceramic sleeve P21, which are disposed within a through-hole P18 of a metallic shell P17, and is fixedly united with these members by means of a rear end portion of the metallic shell P17 being crimped.

Furthermore, the electrode pads P22 provided on the outer surface of a rear end portion of the gas sensor element P1 are in contact with corresponding metal terminals P24 which are connected to respective lead wires P23 extending from an external circuit (not shown), whereby signals of the gas sensor element P1 are output to the external circuit.

[Patent Document 1] Japanese Patent Application Laid-Open (kokai) No. 2010-266429

3. Problems to be Solved by the Invention

Meanwhile, in operation of an internal combustion engine of an automobile or the like, exhaust gas from the engine may cause water, such as water vapor contained therein and condensed water adhering to the inner surface of an exhaust pipe, to adhere to the gas sensor P16. The adhering water may cause a problem in the gas sensor P16 as discussed below.

In the gas sensor P16, the above-mentioned members such as talc P20 isolate a forward end portion of the gas sensor element P1 which is exposed to exhaust gas, from a rear end portion of the gas sensor element P1 where the electrode pads P22, etc., are exposed. However, water may creep along the surface of the gas sensor element P1 (in the direction of the arrow of FIG. 10) from the forward end portion to the rear end portion.

Furthermore, water which has reached the rear end portion of the gas sensor element P1 may permeate along through-holes connected to the corresponding electrode pads P22 exposed at the rear end portion and then along leads disposed between ceramic layers, and may finally reach the electrodes disposed within the forward end portion of the gas sensor element P1.

At this time, if water reaches the reference oxygen chamber P14 via the second outer electrode P8 and the reference electrode P12, water may permeate through the porous insulative protection layer P15. The permeating water may impair insulation between the opposed electrodes P8 and P12 so as to short-circuit the same, and potentially result in hindering gas measurement by the gas sensor P16.

SUMMARY OF THE INVENTION

The present invention has been made to solve the above problem, and an object thereof is to provide a gas sensor in which insulation is ensured between electrodes disposed in a reference oxygen chamber of a gas sensor element.

The above object of the invention has been achieved by providing a gas sensor (1) comprising a gas sensor element. The gas sensor element has a first measuring chamber into which a gas-to-be-measured is introduced via a first diffusion resistor; a second measuring chamber receiving the gas-to-be-measured from the first measuring chamber, from which oxygen has been pumped out or into which oxygen has been pumped in, via a second diffusion resistor; a reference oxygen chamber provided separately from the first measuring chamber and the second measuring chamber and maintained at a predetermined oxygen concentration; a first pump cell which has a first solid electrolyte body and a pair of first electrodes formed on the first solid electrolyte body, a first inner electrode which is one of the paired first electrodes being disposed in the first measuring chamber, a first outer electrode which is the other of the paired first electrodes being disposed externally of the first measuring chamber, the second measuring chamber and the reference oxygen chamber, and which pumps oxygen out of or into the gas-to-be-measured introduced into the first measuring chamber; a second pump cell which has a second solid electrolyte body and a pair of second electrodes formed on the second solid electrolyte body, a second inner electrode which is one of the paired second electrodes being disposed in the second measuring chamber, and a second outer electrode which is the other of the paired second electrodes being disposed in the reference oxygen chamber, and configured such that current flowing between the second inner electrode and the second outer electrode upon operation of the gas sensor element corresponds to the concentration of a particular gas in the second measuring chamber; and an oxygen concentration detection cell which has a third electrolyte body and a pair of third electrodes formed on the third electrolyte body, a detection electrode which is one of the paired third electrodes being disposed in the first measuring chamber, and a reference electrode which is the other of the paired third electrodes being disposed in the reference oxygen chamber. The reference oxygen chamber is formed between the second solid electrolyte body and the third solid electrolyte body. The first measuring chamber is formed between the first solid electrolyte body and the third solid electrolyte body. The gas sensor is characterized in that a gas-permeable, porous, insulative protection layer is formed on at least one of the two electrodes disposed in the reference oxygen chamber, the insulative protection layer being disposed to face the other electrode opposite the one electrode on which the insulative protection layer is formed, or so as to face another insulative protection layer formed on the other electrode, with a gap present therebetween.

According to the present invention, the gas-permeable, porous, insulative protection layer is provided on the surface of at least one of the second outer electrode and the reference electrode disposed on opposite sides (i.e., on a side toward the second pump cell and on a side toward the oxygen concentration detection cell) of the reference oxygen chamber. Also, the insulative protection layer is disposed so as to face the other electrode opposite the one electrode on which the insulative protection layer is formed, or so as to face another insulative protection layer formed on the other electrode, with a gap present therebetween.

As mentioned above, the gas-to-be-measured contains water. However, by virtue of the above structural features, even when the water reaches the second outer electrode and the reference electrode disposed in the reference oxygen chamber, via the through-holes and leads, the water merely stagnates within the electrodes and the insulative protection layer and is unlikely to seep into the gap.

Thus, a short circuit between the two electrodes can be prevented which could otherwise be caused by the water. Therefore, the first mode of the present invention yields the remarkable effect of enabling favorable measurement of a particular gas.

In the case where the insulative protection layer is formed on the surface of only one (e.g., the second outer electrode) of the two electrodes, the gap is provided between the insulative protection layer and the other electrode (e.g., the reference electrode) opposite the one electrode. In the case where the insulative protection layer is formed on the surfaces of the two electrodes, the gap is provided between the two insulative protection layers formed respectively on the surfaces of the two electrodes.

The expression "the other electrode opposite the one electrode" indicates a state in which the one electrode and the other electrode face each other entirely or partially, or a state in which the one electrode and the other electrode are offset from each other in the longitudinal direction of the gas sensor element.

Furthermore, since the insulative protection layer is disposed in the reference oxygen chamber, even when the reference oxygen chamber is deformed in the course of manufacture of the gas sensor, contact between the two electrodes can be prevented. Also, the insulative protection layer can restrain sublimation-induced scattering of a conductive substance (e.g., platinum) contained in the electrodes. Accordingly, deterioration in insulation between the two electrodes can be prevented.

Also, the present invention can be applied to a gas sensor element configured as follows: the first measuring chamber is formed between the first solid electrolyte body which partially constitutes the first pump cell, and the third solid electrolyte body which partially constitutes the oxygen concentration detection cell, and the reference oxygen chamber is formed between the second solid electrolyte body which partially constitutes the second pump cell, and the third solid electrolyte body. In other words, the present invention can be applied to a gas sensor element configured such that the first solid electrolyte body, the first measuring chamber, the third solid electrolyte body, the reference oxygen chamber, and the second solid electrolyte layer are sequentially disposed in layers.

In a preferred embodiment (2) of the gas sensor (1) above, the gas sensor element has a heater overlaid thereon, and the insulative protection layer is formed on the surface of a selected one of the two electrodes disposed in the reference oxygen chamber, the selected electrode being located on a side of the gas sensor element toward the heater.

The electrode located on the side toward the heater is heated to a higher temperature than the opposite electrode. Consequently, at the higher temperature, a conductive substance is more likely to sublime and scatter, to thereby result in a deterioration in electrical insulation. Therefore, by forming the insulative protection layer on the electrode located on the side toward the heater, sublimation-induced scattering of a conductive substance can be effectively restrained.

The "electrode located on the side toward the heater" means an electrode of the two electrodes disposed in the reference oxygen chamber which is closest to the heater. For example, in a gas sensor element in which the first solid electrolyte body, the first measuring chamber, the third solid electrolyte body, the reference oxygen chamber and the second solid electrolyte body are sequentially disposed in layers, when the heater is overlaid on the side toward the second solid electrolyte body, the second outer electrode is an electrode located on the side toward the heater. When the heater is overlaid on the side toward the first solid electrolyte body, the reference electrode is an electrode located on the side toward the heater.

In a preferred embodiment (3) of the gas sensor (2) above, the heater is directly overlaid on the second pump cell on a side opposite the reference oxygen chamber.

By overlaying the heater directly on the second pump cell on the side opposite the reference oxygen chamber, the gas sensor element can be activated in a short period of time. As a result of heating to a higher temperature by the heater, a conductive substance is likely to sublime from the electrode. However, the insulative protection layer can prevent sublimation-induced scattering of the conductive substance.

In a preferred embodiment (4) of the gas sensor (1) above, the insulative protection layer contains alumina having a purity of 99.9% or higher as a main component.

When the purity of alumina is high, usually, the amount of conductive impurities (e.g., Na, Ca and Mg) contained in the alumina is small. Therefore, by use using high-purity alumina for forming the insulative protection layer, even when water soaks into the insulative protection layer and further into the gap, the amount of conductive impurities eluted into the water is small, so that deterioration in electric insulation can be restrained.

The expression "alumina . . . as a main component" means that the insulative protection layer contains alumina in an amount of 50% or more. Additionally, the isolative protection layer may further contain any of zirconia, spinel and titania.

In a preferred embodiment (5) of the gas sensor (1) above, in operation of the gas sensor element, a potential difference develops across the two electrodes disposed in the reference oxygen chamber.

This feature means that in operation of the gas sensor, the two electrodes assume different electric potentials. In a gas sensor element having a potential difference between the two electrodes, when the two electrodes are short-circuited, the electrodes fail to maintain their respective electrical potentials. As a result, a leakage current flows between the electrodes, potentially resulting in a failure to accurately measure a particular gas concentration. However, by providing the insulative protection layer as in the case of the present invention, even a gas sensor having a potential difference between the two electrodes can accurately measure a particular gas concentration.

In a preferred embodiment (6) of the gas sensor (1) above, a dimension of the gap as measured in a facing direction of the two electrodes disposed in the reference oxygen chamber is greater than a thickness of the entire insulative protection layer disposed in the reference oxygen chamber.

By specifying the dimension of the gap as described above, a short circuit which could otherwise be caused by water can be reliably prevented. The "thickness of the entire insulative protection layer" means the following thickness: in the case where the insulative protection layer is formed on the surface of only one electrode (e.g., the second outer electrode), the thickness is the thickness of the insulative protection layer formed on the surface of the one electrode. In the case where the insulative protection layer is formed on the surfaces of each of the two electrodes, the thickness is the total thickness of the two insulative protection layers formed respectively on the surfaces of the two electrodes.

Preferably, the thickness of the insulative protection layer to be laminated on the electrode is one-half or more the thickness of the electrode, so as to effectively restrain sublimation-induced scattering of a conductive substance. However, when the total thickness of the electrode and the insulative protection layer exceeds 100 μm, in the course of firing, the electrode and the insulative protection layer are likely to be deformed and thus encounter difficulty in lamination. Therefore, the thickness of the insulative protection layer is preferably 100 μm or less.

DESCRIPTION OF REFERENCE NUMERALS

Reference numerals used to identify varies features of the invention include the following:
7, 201, 301: gas sensor element
65: heater
69: first solid electrolyte body
73, 205, 305: third solid electrolyte body
77, 209, 309: second solid electrolyte body
83: first pump cell
85: oxygen concentration detection cell
87: second pump cell
89: first measuring chamber
91: first diffusion resistor
93: second diffusion resistor
95: second measuring chamber
99: first outer electrode
101: first inner electrode
109: detection electrode
111, 207, 307: reference electrode
113, 203, 303: reference oxygen chamber
115: second inner electrode
117, 211, 311: second outer electrode
165, 213, 215, 313: insulative protection layer
167, 217, 315: gap

DETAILED DESCRIPTION OF THE PREFERRED EMBODIMENTS

The present invention will next be described in greater detail with reference to the drawings. However, the present invention should not be construed as being limited thereto.

A gas sensor having a gas sensor element of the present invention will be described with reference to an NOx sensor which is fixed to an exhaust pipe of an internal combustion engine for measuring the concentration of nitrogen oxides (NOx).

First Embodiment a) First, the configuration of the gas sensor (hereinafter, referred to as the NOx sensor) of the present embodiment will be described with reference to FIG. 1.

Figure 1:
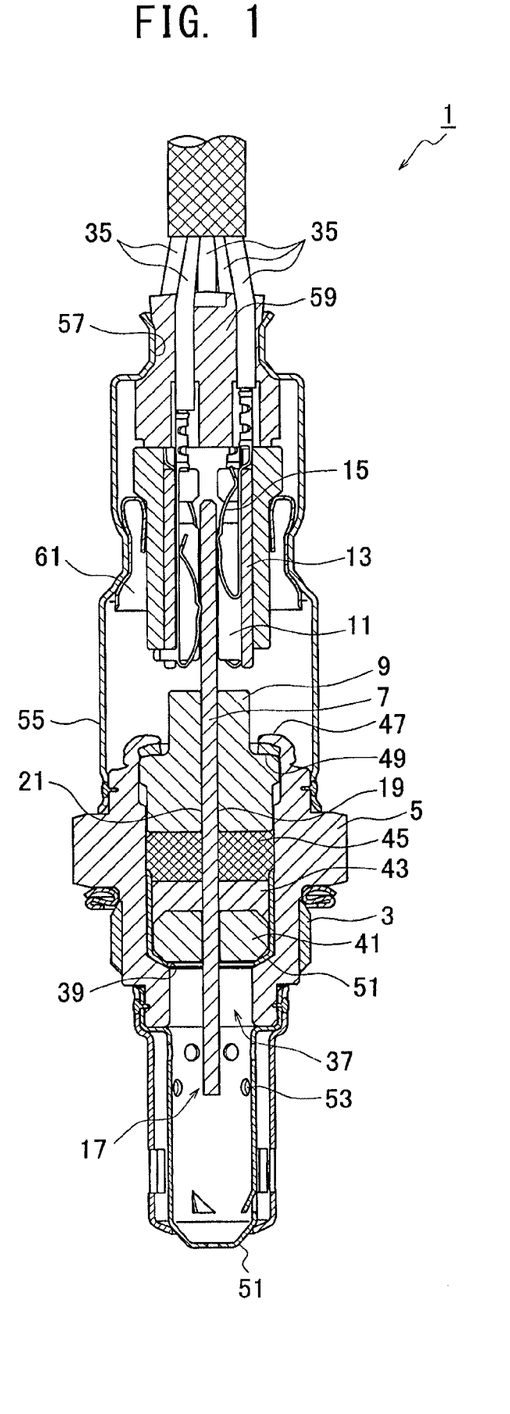
FIG. 1 is a sectional view of an NOx sensor of a first embodiment taken along the axial direction.

In the following description, the downward direction (lower side) in FIG. 1 is called the forward direction (forward side) of the NOx sensor, and the upward direction (upper side) in FIG. 1 is called the rearward direction (rear side) of the NOx sensor.

As shown in FIG. 1, an $NO_x$ sensor 1 of the present embodiment includes a tubular metallic shell 5 which has a threaded portion 3 formed on its outer surface for fixation to an exhaust pipe; a detection element (hereinafter, referred to as the gas sensor element) 7 inserted through the metallic shell 5; a tubular ceramic sleeve 9 disposed so as to radially surround the gas sensor element 7; an insulative separator 13 which has an element insertion hole 11 extending therethrough in the axial direction (in the vertical direction in FIG. 1); and six lead frames 15 (illustrated only partially in FIG. 1) connected to the gas sensor element 7.

The configurational features of the gas sensor will now be described.

The gas sensor element 7 is a plate-like laminate member extending in the axial direction. The gas sensor element 7 has a detection portion 17 formed at its forward end portion (lower end portion in FIG. 1), which is exposed to a gas-to-be-measured; i.e., exhaust gas, and electrode pads 23, 25, 27, 29, 31 and 33 (see FIG. 2) formed on a first plate surface 19 and a second plate surface 21, respectively, which are opposite surfaces of its rear end portion (upper end portion in FIG. 1).

The insulative separator 13 is formed from an insulative material, such as alumina, and has the element insertion hole 11 for accommodating at least a portion of the gas sensor element 7 and the lead frames 15.

The insulative separator 13 holds the lead frames 15 and the gas sensor element 7 within the element insertion hole 11, whereby the lead frames 15 are electrically connected to respective electrode pads 23 to 33 of the gas sensor element 7. The lead frames 15 are also electrically connected to respective lead wires 35 extending into the gas sensor from outside the gas sensor, thereby forming current paths for current which flows between the electrode pads 23 to 33 and external equipment to which the lead wires 35 are connected.

The metallic shell 5 is a metal member formed from, for example, stainless steel and has a substantially tubular shape. The metallic shell 5 has a through-hole 37 extending therethrough in the axial direction and a ledge 39 projecting radially inward within the through-hole 37.

The metallic shell 5 is configured to hold the gas sensor element 7 such that the detection portion 17 protrudes from the forward end of the through-hole 37, and the electrode pads 23 to 33 are disposed externally of the rear end of the through-hole 37.

An annular ceramic holder 41, powder filler layers (talc rings) 43 and 45, and the above-mentioned ceramic sleeve 9 are stacked in this order from the forward side to the rear side within the through-hole 37 of the metallic shell 5 so as to radially surround the gas sensor element 7.

Also, a crimp ring 49 is disposed between the ceramic sleeve 9 and a rear end portion 47 of the metallic shell 5. A metal cup 51 is disposed between the ceramic holder 41 and the ledge 39 of the metallic shell 5. The rear end portion 47 of the metallic shell 5 is crimped so as to press the ceramic sleeve 9 forward via the crimp ring 49.

A tubular protector 51 formed from, for example, stainless steel is disposed at the forward side of the metallic shell 7 so as to cover a forward end portion of the gas sensor element 7. The protector 51 has gas communication holes 53 for allowing exhaust gas to pass therethrough. The protector 51 has a dual structure consisting of an inner protector and an outer protector.

Meanwhile, a tubular sheath 55 formed from, for example, stainless steel is fixed to a rear end portion of the metallic shell 7. A rear end opening 57 of the tubular sheath 55 is closed with a grommet 59 formed from, for example, a fluororubber.

The insulative separator 13 is held within the tubular sheath 55 by means of a holding member 61 fixed (by crimping) to the inside of the tubular sheath 55, in such a manner that its rear end is in contact with the grommet 59.

b) Next, the gas sensor element 7 of the present embodiment will be described.

Figure 2:
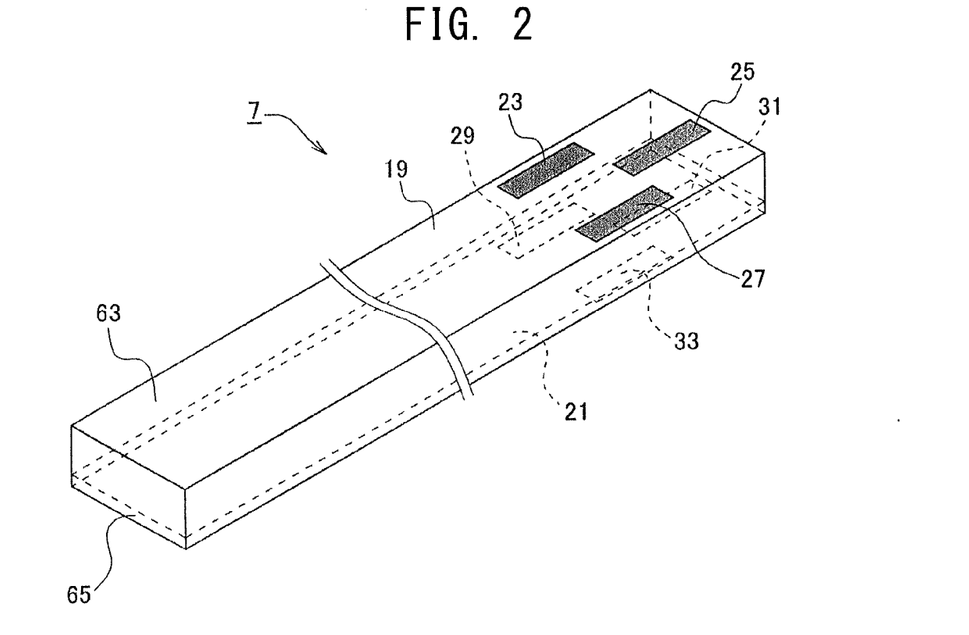
FIG. 2 is a perspective view showing a gas sensor element with a portion along the axial direction omitted.

As shown in FIG. 2, the gas sensor element 7 includes a plate-like element section 63 extending in the axial direction (in the left-right direction in FIG. 2) and a plate-like heater 65 extending in the axial direction. The gas sensor element 7 is formed into a plate-like shape which has a rectangular cross section and in which the element section 63 and the heater 65 are laminated together.

First, the configuration of a forward end portion of the gas sensor element 7 will be described.

Figure 3:
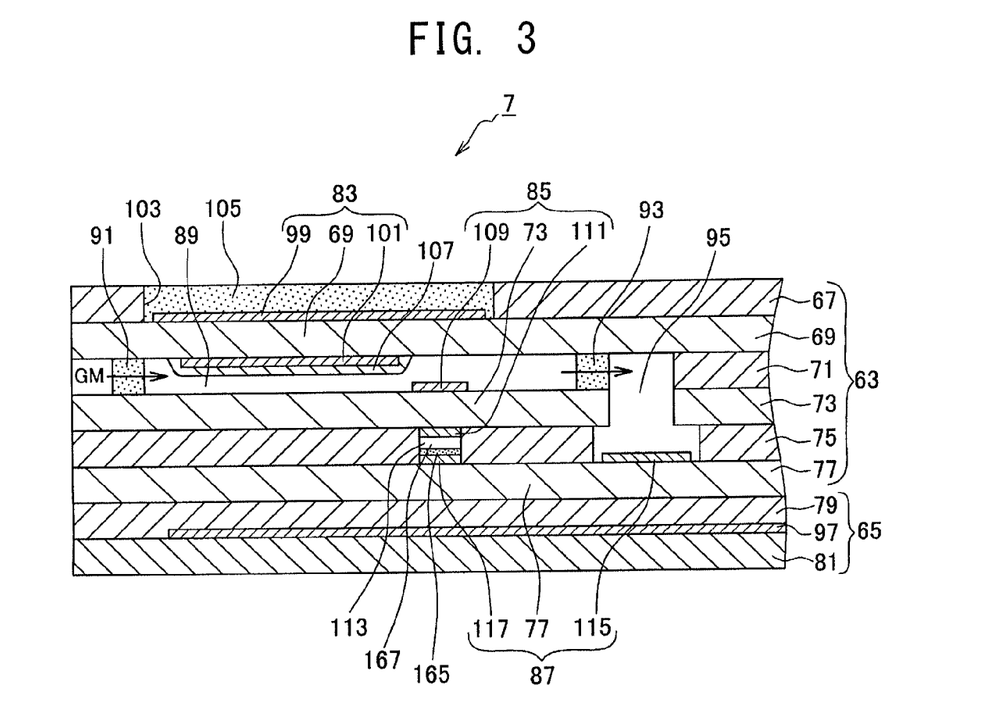
FIG. 3 is an explanatory view showing, on an enlarged scale, in section taken along the thickness direction, the inner structure of a forward end portion of the gas sensor element.

FIG. 3 shows, on an enlarged scale, in section, a forward end portion of the gas sensor element 7. As shown in FIG. 3, the gas sensor element 7 is a laminate of, from the top of FIG. 3, an insulation layer 67, a first solid electrolyte body 69, an insulation layer 71, a third solid electrolyte body 73, an insulation layer 75, a second solid electrolyte body 77, and insulation layers 79 and 81. Particularly, as described below, a first pump cell 83, a second pump cell 87, and an oxygen concentration detection cell 85 are configured, using the first to third solid electrolyte bodies 69, 77 and 73, respectively, as their main members.

The configurational features of the gas sensor element 7 will now be described.

A first measuring chamber 89 is formed between the first solid electrolyte body 69 and the third solid electrolyte body 73. A first diffusion resistor 91 is disposed at the left end (inlet) of the first measuring chamber 89. A gas-to-be-measured (GM), e.g., exhaust gas, is introduced into the first measuring chamber 89 via the first diffusion resistor 91. A second diffusion resistor 93 is disposed at an end of the first measuring chamber 89 opposite the inlet.

A second measuring chamber 95 is formed at the right of the first measuring chamber 89 (i.e., at the right of the second diffusion resistor 93) and communicates with the first measuring chamber 89 via the second diffusion resistor 93. The second measuring chamber 95 is formed between the first solid electrolyte body 69 and the second solid electrolyte body 77 while extending through the third solid electrolyte body 73.

The first to third solid electrolyte bodies 69, 77 and 73 contain oxygen-ion-conductive zirconia as a main component. The insulation layers 67, 71, 75, 79 and 81 contain alumina as a main component. The first and second diffusion resistors 91 and 95 are formed from a porous material of, for example, alumina. The main component is "a component material which is contained in an amount of 50 wt % or more in the individual ceramic layers."

A resistance heating body 97 is embedded between the insulation layers 79 and 81. The resistance heating body 97 is formed from, for example, platinum and extends along the longitudinal direction (horizontal direction in FIG. 3). The insulation layers 79 and 81 and the resistance heating body 97 sandwiched therebetween constitute the heater 65. The heater 65 heats the gas sensor element 7 to a predetermined activation temperature for enhancing oxygen ion conductivity of the solid electrolyte bodies 69, 77 and 73, to thereby stabilize operation.

The first pump cell 83 includes the first solid electrolyte body 69 and a pair of first electrodes 99 and 101 disposed with the first solid electrolyte body 69 sandwiched therebetween; i.e., a pair consisting of a first outer electrode 99 and a first inner electrode 101 (a counter electrode of the first outer electrode 99). The first outer electrode 99 and the first inner electrode 101 predominantly contain platinum.

The first outer electrode 99 is covered with a gas-permeable (e.g., oxygen-permeable) porous layer 105 (formed from, for example, alumina) fitted in an opening portion 103 of the insulation layer 67. The first inner electrode 101 faces the first measuring chamber 89 and is covered with a gas-permeable porous layer 107.

The oxygen concentration detection cell 85 includes the third solid electrolyte body 73 and a pair of third electrodes 109 and 111 disposed with the third solid electrolyte body 73 sandwiched therebetween; i.e., a pair consisting of a detection electrode 109 and a reference electrode 111. The detection electrode 109 faces the first measuring chamber 89 at a position located downstream (in FIG. 3, at the right) of the first inner electrode 101. The reference electrode 111 is disposed in a reference oxygen chamber 113, which will be described below. The detection electrode 109 and the reference electrode 111 predominantly contain platinum.

The insulation layer 75 has a cutout for allowing the reference electrode 111 in contact with the third solid electrolyte body 73 to be disposed therein. That is, as described in detail below, the cutout defines the reference oxygen chamber 113 sandwiched between the third solid electrolyte body 73 and the second solid electrolyte body 77.

The second pump cell 87 includes the second solid electrolyte body 77 and a pair of second electrodes 115 and 117 formed on one side of the second solid electrolyte body 77. The electrode 115 of the two second electrodes 115 and 117 is a second inner electrode 115 disposed on a surface of the second solid electrolyte body 77 which faces the second measuring chamber 95. The other electrode 117 of the two second electrodes 115 and 117 is a second outer electrode 117 (a counter electrode of the second inner electrode 115) disposed on a surface of the second solid electrolyte body 77 which faces the reference oxygen chamber 113. The second inner electrode 115 and the second outer electrode 117 predominantly contain platinum.

Next, the configuration of a rear end portion of the gas sensor element 7 will be described.

Figure 4:
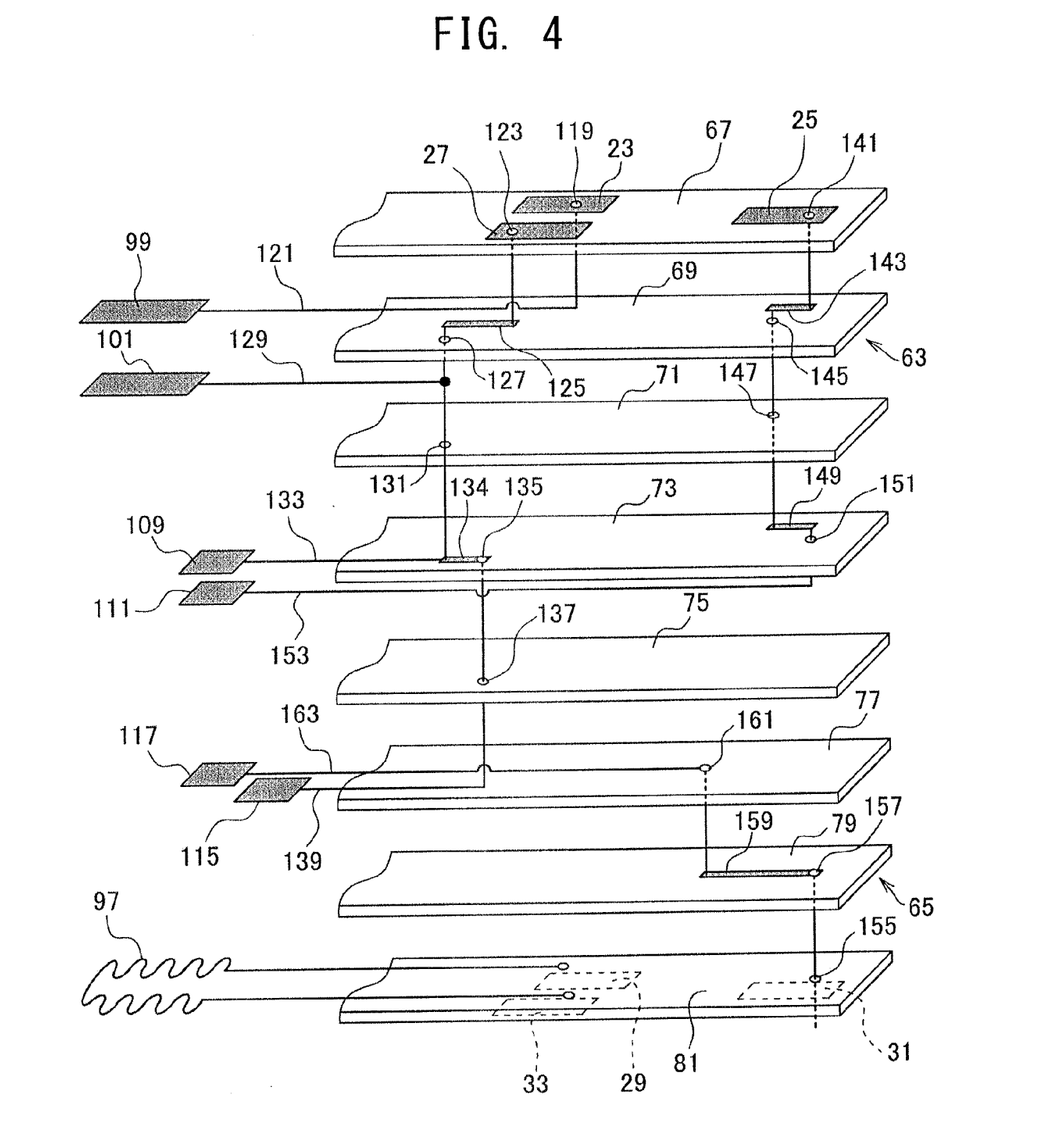
FIG. 4 is a partially exploded perspective view showing the gas sensor element.

As shown in an exploded fashion in FIG. 4 and as mentioned above, the electrode pads 23, 25 and 27 are formed on a surface of a rear end portion (in FIG. 4, a right end portion) of the element section 63 of the gas sensor element 7 on a side opposite the heater 65 (in FIG. 4, on the upper side).

The electrode pad 23 is connected to the first outer electrode 99 via a conductor in a through-hole 119 provided in the insulation layer 67 and a lead 121 on the first solid electrolyte body 69.

The electrode pad 27 is connected to the first inner electrode 101 via a conductor in a through-hole 123 provided in the insulation layer 67, a lead 125 on the first solid electrolyte body 69, a conductor in a through-hole 127 provided in the first solid electrolyte body 69, and a lead 129 on the first solid electrolyte body 69 (on the back side of the first solid electrolyte body 69).

The electrode pad 27 is also connected to the detection electrode 109 via the conductor in the through-hole 123 provided in the insulation layer 67, the lead 125 on the first solid electrolyte body 69, the conductor in the through-hole 127 provided in the first solid electrolyte body 69, a conductor in a through-hole 131 provided in the insulation layer 71, and a lead 133 on the third solid electrolyte body 73.

The electrode pad 27 is further connected to the second inner electrode 115 via the conductor in the through-hole 123 provided in the insulation layer 67, the lead 125 on the first solid electrolyte body 69, the conductor in the through-hole 127 provided in the first solid electrolyte body 69, the conductor in the through-hole 131 provided in the insulation layer 71, a lead 134 on the third solid electrolyte body 73, a conductor in a through-hole 135 provided in the third solid electrolyte body 73, a conductor in a through-hole 137 provided in the insulation layer 75, and a lead 139 on the second solid electrolyte body 77.

That is, the inner electrode 101, the detection electrode 109, and the second inner electrode 115 have the same electrical potential.

The electrode pad 25 is connected to the reference electrode 111 via a conductor in a through-hole 141 provided in the insulation layer 67, a lead 143 on the first solid electrolyte body 69, a conductor in a through-hole 145 provided in the first solid electrolyte body 69, a conductor in a through-hole 147 provided in the insulation layer 71, a lead 149 on the third solid electrolyte body 73, a conductor in a through-hole 151 provided in the third solid electrolyte body 73, and a lead 153 provided on the third solid electrolyte body 73 (on the back side of the third solid electrolyte body 73).

Meanwhile, as mentioned above, the electrode pads 29, 31, 33 are formed on a surface of a rear end portion of the gas sensor element 7 on a side toward the heater 65 (in FIG. 4, on the lower side).

The electrode pad 31 is connected to a second outer electrode 117 via a conductor in a through-hole 155 provided in the insulation layer 81, a conductor in a through-hole 157 provided in the insulation layer 79, a lead 159 on the insulation layer 79, a conductor in a through-hole 161 provided in the second solid electrolyte body 77, and a lead 163 on the second solid electrolyte body 77.

The electrode pads 29 and 33 are connected to the respective opposite ends of the resistance heating body 97.

Next, the configuration of the reference oxygen chamber 113, which is an essential feature of the present embodiment, will be described.

Figure 5:
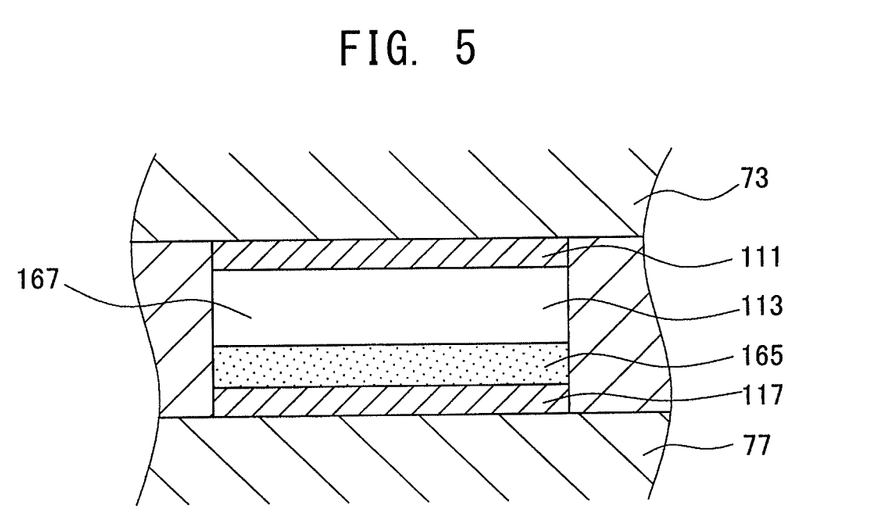
FIG. 5 is an explanatory view showing, on an enlarged scale, in section taken along the thickness direction, a reference oxygen chamber.

FIG. 5 shows, on an enlarged scale, in a section taken along the thickness direction, the reference oxygen chamber 113. As shown in FIG. 5, the reference oxygen chamber 113 is a space assuming the shape of a rectangular parallelepiped; the reference electrode 111 is disposed on a wall surface (in FIG. 5, an upper wall surface) of the reference oxygen chamber 113 on the side toward the third solid electrolyte body 73; and the second outer electrode 117 is disposed opposite the reference electrode 111, on a wall surface (in FIG. 5, a lower wall surface) of the reference oxygen chamber 113 on the side toward the second solid electrolyte body 77.

Particularly, in the present embodiment, a porous, insulative protection layer 165 formed from, for example, alumina having a purity of 99.9% or higher, which is electrically insulative, is formed so as to cover the entire surface of the second outer electrode 117. A gap 167, which is a hollow space, is present between the reference electrode 111 and the insulative protection layer 165.

The thicknesses of the reference electrode 111 and the second outer electrode 117 (as measured in the vertical direction in FIG. 5) are, for example, 5 μm to 15 μm (e.g., 10 μm). The thickness of the insulative protection layer 165 is, for example, 5 μm to 40 μm. The thickness of the gap 167 is, for example, 20 μm to 50 μm. The thickness of the gap 167 is set greater than that of the insulative protection layer 165.

c) Next, a method of manufacturing the gas sensor element 7 of the present embodiment will briefly be described.

Although unillustrated, in manufacture of the gas sensor element 7 of the present embodiment, as well known, among the above-mentioned eight layers, the six layers 67, 69, 73, 77, 79 and 81 are formed by use of respective ceramic sheets (of, for example, zirconia or alumina). The two insulative layers 71 and 75 are formed on the respective ceramic sheets by screen printing. The ceramic sheets which will become the layers 67, 69, 73, 77, 79 and 81 have through-holes formed therein at required positions.

Furthermore, in order to form the electrodes, 99, 101, 109, 111, 117 and 115 and the leads 121, 125, 143, 129, 133, 149, 163, 139 and 159, electrode patterns and lead patterns are formed on the surfaces of the corresponding layers (by use of, for example, a platinum paste). In order to form the electrode pads 23 to 33, electrode pad patterns are formed on the surfaces of the corresponding layers.

Particularly, in the present embodiment, an electrode pattern which will become the second outer electrode 117 is formed on the surface of a ceramic sheet which will become the second solid electrolyte body 77, at a position corresponding to the reference oxygen chamber 113. Subsequently, a pore forming layer which will become the insulative protection layer 165 is formed on the electrode pattern by screen printing a pore promoting paste (which contains a pore forming material that will generate pores upon firing). Furthermore, vanishing paste containing a vanishing (or rather vaporizing) material which vanishes upon firing is screen-printed on the profuseness formation layer, thereby forming a gap formation layer. For example, alumina can be used as the pore forming material. For example, carbon powder can be used as the vanishing material.

The above-described ceramic sheets (having the layers formed thereon by screen printing) are laminated together, thereby yielding a laminate. The laminate is fired, to thereby yield the gas sensor element 7. In the course of firing, the pore forming layer becomes the insulative protection layer 165, and the gap formation layer burns and vanishes, thereby yielding the gap 167.

d) Next the configuration of a sensor control unit for controlling the operation of the gas sensor element 7 will be described.

Figure 6:
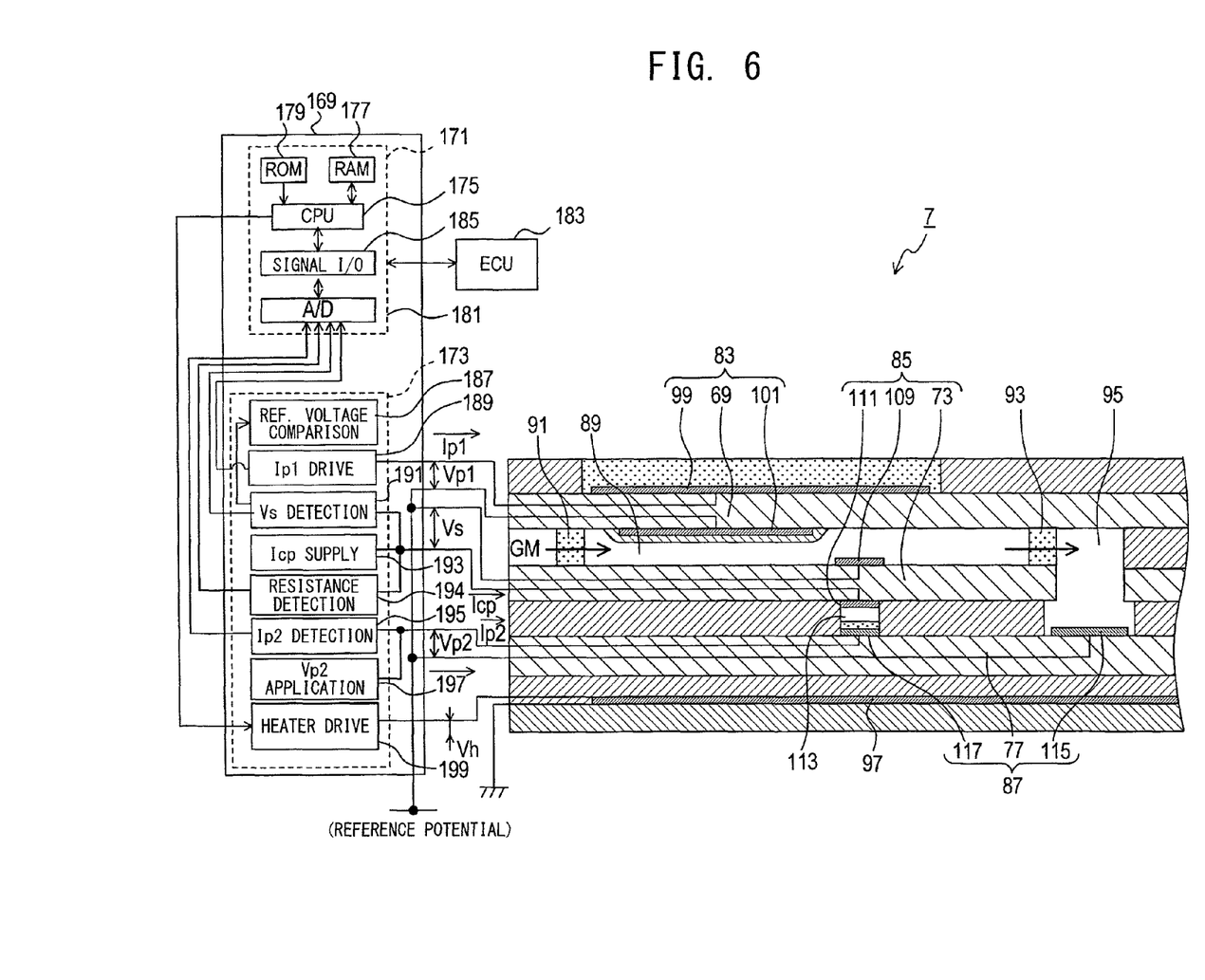
FIG. 6 is an explanatory view showing an electrical configuration of a sensor control unit connected to the gas sensor element.

As shown in FIG. 6, a sensor control unit 169 for controlling the operation of the gas sensor element 7 has a microcomputer 171, an electric circuit section 173, etc.

The microcomputer 171 includes a CPU 175 for executing various arithmetic operations; a RAM 177 for storing the results of the arithmetic operations, etc.; and a ROM 179 for storing programs which the CPU 175 executes, etc. The microcomputer 171 further includes an A/D converter 181; a signal input-output section 185 connected to the electric circuit section 173 via the A/D converter 181 adapted to communicate with an electronic control unit (hereinafter, referred to as the ECU) 183; and an unillustrated timer clock.

The electric circuit section 173 is composed of a reference voltage comparison circuit 187; an Ip1 drive circuit 189; a Vs detection circuit 191; an Icp supply circuit 193; a resistance detection circuit 194; an Ip2 detection circuit 195; a Vp2 application circuit 197; and a heater drive circuit 199. Under control of the microcomputer 171, the electric circuit section 173 detects the $NO_x$ concentration in exhaust gas by use of the gas sensor element 7.

The first inner electrode 101 of the first pump cell 83 exposed to the first measuring chamber 89, the detection electrode 109 of the oxygen concentration detection cell 85 exposed to the first measuring chamber 89, and the second inner electrode 115 of the second pump cell 87 exposed to the second measuring chamber 95 are connected to a reference potential. One of the two electrodes of the resistance heating body 97 is grounded.

e) Next the operation of detecting the $NO_x$ concentration in exhaust gas by the thus-configured sensor control unit 169 will be described.

As shown in FIG. 6, the first to third electrolyte bodies 69, 77 and 73 of the gas sensor element 7 are heated and activated in association with an increase in temperature of the resistance heating body 97 to which the heater drive circuit 199 applies a drive current. Accordingly, the first pump cell 83, the oxygen concentration detection cell 85, and the second pump cell 87 are heated to an activation temperature at which the cells will operate.

Exhaust gas is introduced into the first measuring chamber 89 while its flow rate is limited by the first diffusion resistor 91. The Icp supply circuit 193 applies a very weak current Icp to the oxygen concentration detection cell 85 such that the current Icp flows from the reference electrode 111 to the detection electrode 109. Thus, oxygen in exhaust gas can receive electrons from the detection electrode 109 having a negative polarity and that is disposed in the first measuring chamber 89, to thereby form oxygen ions. The oxygen ions flow through the third solid electrolyte body 73 into the reference oxygen chamber 113. That is, by means of the current Icp flowing between the detection electrode 109 and the reference electrode 111, oxygen in the first measuring chamber 89 is fed into the reference oxygen chamber 113.

The Vs detection circuit 191 detects voltage between the detection electrode 109 and the reference electrode 111; the reference voltage comparison circuit 187 compares the detected voltage with a reference voltage (425 mV); and the result of the comparison is output to the Ip1 drive circuit 189. By adjusting the oxygen concentration in the first measuring chamber 89 so that the potential difference between the detection electrode 109 and the reference electrode 111 is fixed at around 425 mV, the oxygen concentration of exhaust gas in the first measuring chamber 89 approaches a predetermined value (e.g., $10^{-8}$ atm to $10^{-9}$ atm).

When the oxygen concentration of exhaust gas introduced into the first measuring chamber 89 is lower than the predetermined value, the Ip1 drive circuit 189 applies a current Ip1 to the first pump cell 83 such that the first outer electrode 99 has a negative polarity, thereby pumping oxygen into the first measuring chamber 89 from outside the gas sensor element 7. When the oxygen concentration of exhaust gas introduced into the first measuring chamber 89 is higher than the predetermined value, the Ip1 drive circuit 189 applies the current Ip1 to the first pump cell 83 such that the first inner electrode 101 has a negative polarity, thereby pumping out oxygen from the first measuring chamber 89 to the outside of the gas sensor element 7.

In this manner, exhaust gas whose oxygen concentration has been adjusted in the first measuring chamber 89 is introduced into the second measuring chamber 95 via the second diffusion resistor 93. By means of the Vp2 application circuit 197 applying a voltage Vp2 between the second outer electrode 117 and the second inner electrode 115, $NO_x$ contained in exhaust gas which has come into contact with the second inner electrode 115 in the second measuring chamber 95 is decomposed (reduced) into $N_2$ and $O_2$ on the second inner electrode 115. The oxygen thus formed assumes the form of oxygen ions, and the oxygen ions flow through the second solid electrolyte body 77 into the reference oxygen chamber 113. Thus, current which flows through the second pump cell 87 corresponds to the $NO_x$ concentration.

Therefore, in the sensor control unit 169, the Ip2 detection circuit 195 detects a current Ip2 which flows through the second pump cell 87, and, on the basis of the detected current Ip2, the $NO_x$ concentration in exhaust gas is detected.

More specifically, the relationship between the $NO_x$ concentration and the current Ip2 is obtained beforehand, and an associated map or the like is prepared. The $NO_x$ concentration corresponding to the measured current Ip2 is obtained from the map.

f) As mentioned above, in the present embodiment, the reference electrode 111 of the oxygen concentration detection cell 85 and the second outer electrode 117 of the second pump cell 87 are disposed opposite each other on opposing sides of the reference oxygen chamber 113 of the gas sensor element 7. Furthermore, the gas-permeable, porous, insulative protection layer 165 is formed on the surface of the second outer electrode 117, and the insulative protection layer 165 is disposed opposite the reference electrode 111 with the gap 167 present therebetween.

By virtue of the above configurational features, even when water contained in exhaust gas reaches the reference electrode 111 and the second outer electrode 117 disposed in the reference oxygen chamber 113, via the through-holes 141, 145, 151, 161, 157 and 155 and the leads 146, 149, 153, 163 and 159, the water merely stagnates within the electrodes 111 and 117 and the insulative protection layer 164 and is unlikely to seep into the gap 167 between the reference electrode 111 and the insulative protection layer 165.

Thus, since a short circuit between the two electrodes 111 and 117 can be prevented which could otherwise occur due to the water, the two electrodes 111 and 117 can maintain their respective predetermined electrical potentials. Therefore, measurement of the $NO_x$ concentration can proceed without being hindered by the presence of water in the exhaust gas.

Particularly, in the present embodiment, as mentioned above, in measuring the $NO_x$ concentration, a predetermined potential difference (Vs−Vp2) exists between the two electrodes 111 and 117 disposed in the reference oxygen chamber 113. Therefore, it is important to prevent the occurrence of a short circuit. When the two electrodes 111 and 117 are short-circuited, current flows between the two electrodes 111 and 117. As a result, the output value of the current Ip2 increases, resulting in a failure to accurately measure the concentration of gas-to-be-measured.

Also, in the present embodiment, the insulative protection layer 165 is formed on the surface of the second outer electrode 117, which is, of the two electrodes 111 and 117 disposed in the reference oxygen chamber 113, the one located on the side toward the heater 65. Thus, even when a conductive substance contained in the second outer electrode 117; e.g., Pt, is sublimed as a result of heating by the heater 65, the sublimed Pt is sufficiently trapped in the insulative protection layer 165, whereby scattering of sublimed Pt into the gap 167 can be effectively restrained.

Furthermore, in the present embodiment, since the insulative protection layer 165 is formed from alumina having a purity of 99.9% or higher, even when water seeps into the insulative protection layer 165 and further into the gap 167, the amount of conductive impurities eluted into the water from the insulative protection layer 165 is small. Also from this aspect, deterioration in electric insulation can be restrained.

The present embodiment uses an insulative protection layer 165 formed from alumina. However, the insulative protection layer 165 may contain a ceramic material, such as spinel, titania, or zirconia, in place of alumina as a main component.

Additionally, in the present embodiment, the thickness of the gap 167 in the reference oxygen chamber 113 is greater than that of the insulative protection layer 165, whereby a water-induced short circuit can be reliably prevented.

g) Next an experiment conducted to verify the effects of the present invention will be described.

Figure 7A:
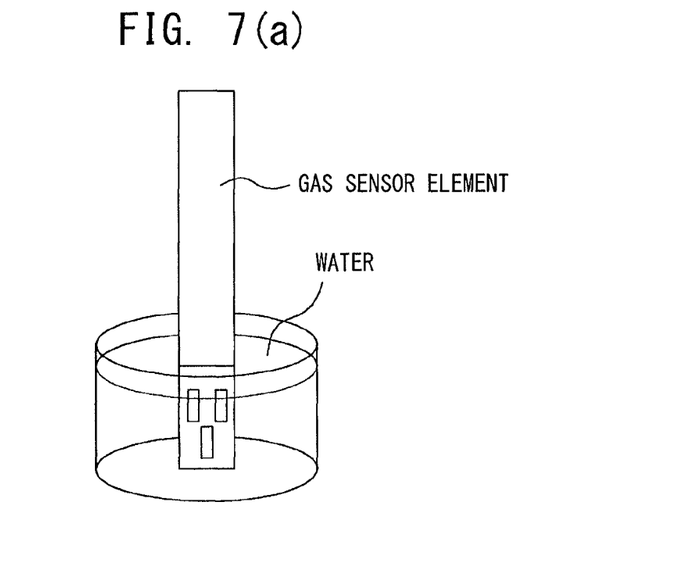
FIG. 7(a) is an explanatory view showing the method of an experiment in which a rear end portion of the gas sensor element is immersed in water.

In the present experiment, six gas sensor elements (sample Nos. 1 to 6) similar to that of the first embodiment were prepared as examples of the present invention. As shown in FIG. 7(a), each of the gas sensor elements was immersed in water for a predetermined time (e.g., 36 hours) in such a manner that all of the electrode pads disposed on its rear end portion were immersed in water.

Subsequently, the gas sensor elements were activated at room temperature (25° C.) in the air, and the current Ip2 was measured. The results of the measurement are shown in Table 1 below and in FIG. 7(b).

Meanwhile, sample Nos. 7 to 10 were prepared as comparative examples outside the scope of the present invention. Each of the gas sensor elements of the comparative examples was immersed in water for the predetermined time in such a manner that all of the electrode pads disposed on its rear end portion were immersed in water. Subsequently, the gas sensor elements were activated at room temperature (25° C.) in the air, and the current Ip2 was measured. The results of the measurement are shown in Table 1 below and in FIG. 7(b).

Sample Nos. 7 to 10 are gas sensor elements having no gap in the reference oxygen chamber; namely, the gap of the reference oxygen chamber is filled with an insulative protection layer.

TABLE 1

| | | Current Ip2 [μA] | |
|---|---|---|---|
| Sample No. | | Initial stage | After 36 hours |
| Example | 1 | 0 | 0.0021 |
| | 2 | 0 | 0.0019 |
| | 3 | 0 | 0.0031 |
| | 4 | 0 | 0.0026 |
| | 5 | 0 | 0.0012 |
| | 6 | 0 | 0.0056 |
| Comparative example | 7 | 0 | 0.3234 |
| | 8 | 0 | 0.1457 |
| | 9 | 0 | 0.09 |
| | 10 | 0 | 0.054 |

Figure 7B:
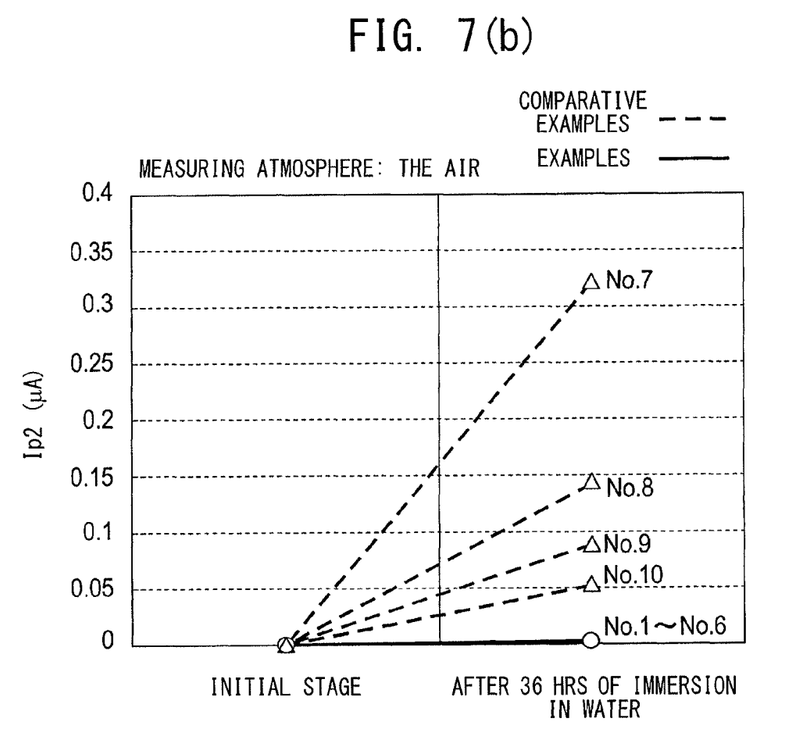
FIG. 7(b) is an graph showing the results of the experiment.

As is apparent from Table 1 above and FIG. 7(b), sample Nos. 1 to 6 of the present invention exhibited a current Ip2 of 0.0056 μA or less after immersion in water for 36 hours, indicating excellent durability (electrical insulation).

In contrast, sample Nos. 7 to 10 of the comparative examples exhibited a current Ip2 of 0.054 μA or greater after immersion in water for 36 hours, indicating low durability, which is unfavorable.

Second Embodiment

A second embodiment of the present invention will next be described. Description of features similar to those of the first embodiment is omitted.

Since a gas sensor element of the second embodiment differs from that of the first embodiment only in the configuration of the reference oxygen chamber, the configuration of the reference oxygen chamber is described.

Figure 8A:
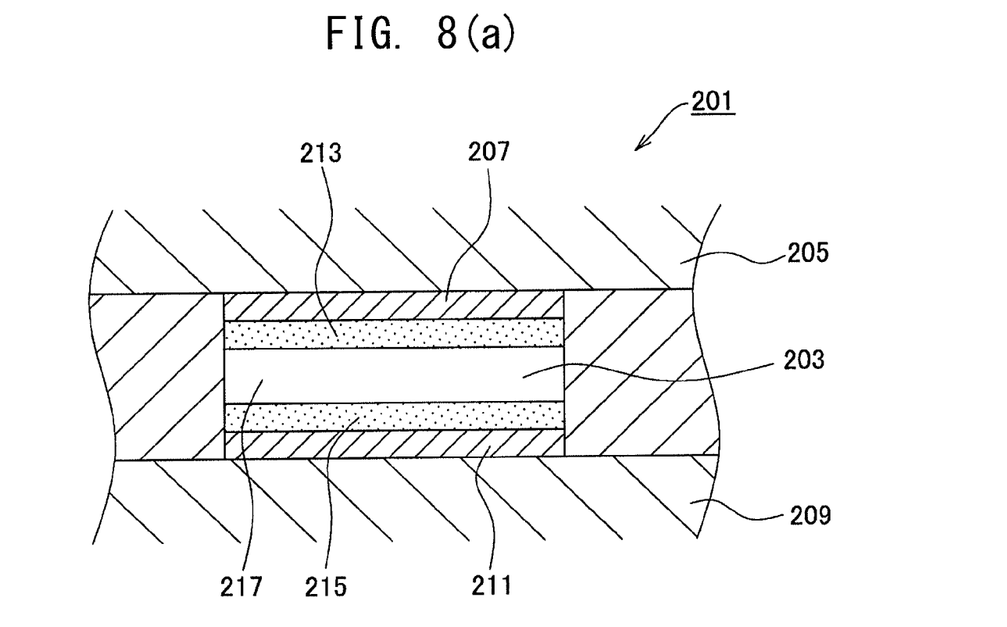
FIG. 8(a) is an explanatory view showing, on an enlarged scale, in section taken along the thickness direction, the reference oxygen chamber of a gas sensor element of a second embodiment.

As shown in FIG. 8(a), similar to the first embodiment, a reference oxygen chamber 203 of a gas sensor element 201 of the present embodiment has a reference electrode 207 formed on a surface of a third solid electrolyte body 205 (located at the upper side of FIG. 8(a)), and a second outer electrode 211 formed on a surface of a second solid electrolyte body 209 (located at the lower side of FIG. 8(a)).

Particularly, in the present embodiment, a porous first insulative protection layer 213 is formed so as to cover the surface of the reference electrode 207, and a similar porous second insulative protection layer 215 is formed so as to cover the surface of the second outer electrode 211.

Furthermore, a gap 217, which is a hollow space, is present between the first insulative protection layer 213 and the second insulative protection layer 215.

The second embodiment also yields effects similar to those of the first embodiment.

Third Embodiment

A third embodiment of the present invention will next be described. Description of features similar to those of the first embodiment is omitted.

Since a gas sensor element of the third embodiment differs from that of the first embodiment only in the configuration of the reference oxygen chamber, the configuration of the reference oxygen chamber is described.

Figure 8B:
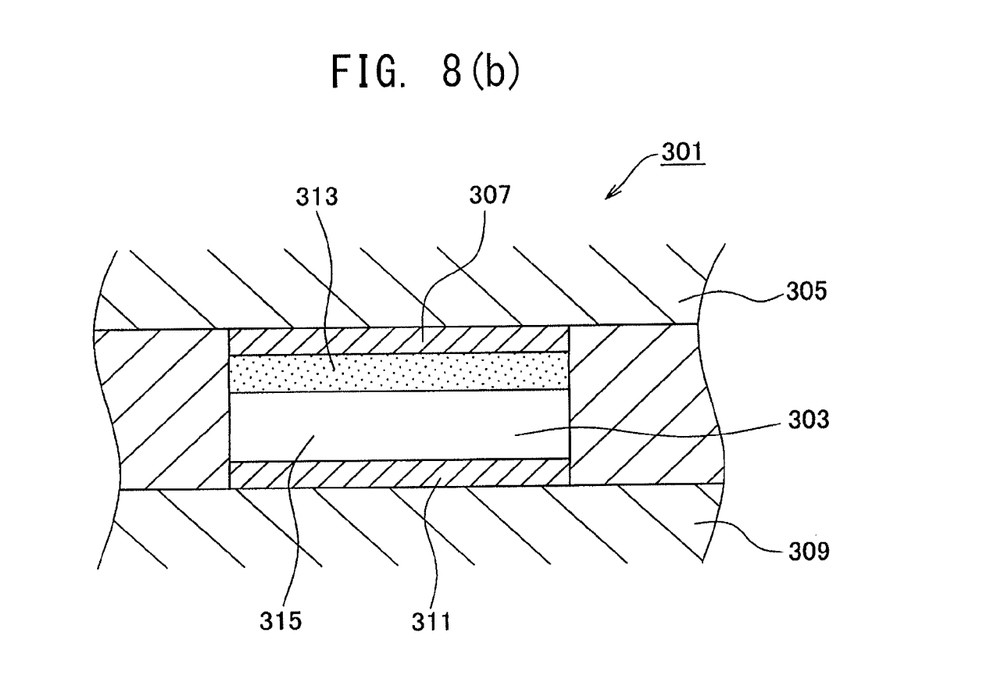
FIG. 8(b) is an explanatory view showing, on an enlarged scale, in section taken along the thickness direction, the reference oxygen chamber of a gas sensor element of a third embodiment.

As shown in FIG. 8(b), similar to the first embodiment, a reference oxygen chamber 303 of a gas sensor element 301 of the present embodiment has a reference electrode 307 formed on a surface of a third solid electrolyte body 305 (located at the upper side of FIG. 8(b)), and a second outer electrode 311 formed on a surface of a second solid electrolyte body 309 (located at the lower side of FIG. 8(b)).

Particularly, in the present embodiment, a porous insulative protection layer 313 is formed so as to cover the surface of the reference electrode 307, and a gap 315, which is a hollow space, is present between the insulative protection layer 313 and the second outer electrode 311.

The third embodiment also yields effects similar to those of the first embodiment.

The invention has been described in detail with reference to the above embodiments. However, the invention should not be construed as being limited thereto. It should further be apparent to those skilled in the art that various changes in the form and detail of the invention as shown and described above may be made. It is intended that such changes be included within the spirit and scope of the claims appended hereto.

This application is based on Japanese Patent Application No. 2011-159950 filed Jul. 21, 2011, incorporated herein by reference in its entirety.

What is claimed is:

1. A gas sensor comprising a gas sensor element, the gas sensor element having:
   a first measuring chamber into which a gas-to-be-measured is introduced via a first diffusion resistor;
   a second measuring chamber receiving the gas-to-be-measured from the first measuring chamber, from which oxygen has been pumped out or into which oxygen has been pumped in, via a second diffusion resistor;
   a reference oxygen chamber provided separately from the first measuring chamber and the second measuring chamber and maintained at a predetermined oxygen concentration;
   a first pump cell which has a first solid electrolyte body and a pair of first electrodes formed on the first solid electrolyte body, a first inner electrode which is one of the paired first electrodes being disposed in the first measuring chamber, a first outer electrode which is the other of the paired first electrodes being disposed externally of the first measuring chamber, the second measuring chamber and the reference oxygen chamber, and which pumps oxygen out of or into the gas-to-be-measured introduced into the first measuring chamber;
   a second pump cell which has a second solid electrolyte body and a pair of second electrodes formed on the second solid electrolyte body, a second inner electrode which is one of the paired second electrodes being disposed in the second measuring chamber, and a second outer electrode which is the other of the paired second electrodes being disposed in the reference oxygen chamber, and configured such that a current flowing between the second inner electrode and the second outer electrode upon operation of the gas sensor element corresponds to the concentration of a particular gas in the second measuring chamber; and
   an oxygen concentration detection cell which has a third electrolyte body and a pair of third electrodes formed on the third electrolyte body, a detection electrode which is one of the paired third electrodes being disposed in the first measuring chamber, and a reference electrode which is the other of the paired third electrodes being disposed in the reference oxygen chamber;
   the reference oxygen chamber being formed between the second solid electrolyte body and the third solid electrolyte body,
   the first measuring chamber being formed between the first solid electrolyte body and the third solid electrolyte body,
   the gas sensor being characterized in that a gas-permeable, porous, insulative protection layer is formed on at least one of the two electrodes disposed in the reference oxygen chamber, the insulative protection layer being disposed to face the other electrode opposite the one electrode on which the insulative protection layer is formed, or so as to face another insulative protection layer formed on the other electrode, with a gap present therebetween,
   wherein:
   the gas sensor element has a heater overlaid thereon,
   the insulative protection layer is formed on the surface of a selected one of the two electrodes disposed in the reference oxygen chamber, the selected electrode being located on a side of the gas sensor element toward the heater, and
   a thickness of the insulative protection layer is from 5 to 40 μm.

2. The gas sensor according to claim 1, wherein the heater is directly overlaid on the second pump cell on a side opposite the reference oxygen chamber.

3. The gas sensor according to claim 1, wherein the insulative protection layer contains alumina having a purity of 99.9% or higher as a main component.

4. The gas sensor according to claim 1, wherein in operation of the gas sensor element, a potential difference develops across the two electrodes disposed in the reference oxygen chamber.

5. The gas sensor according to claim 1, wherein a dimension of the gap as measured in a facing direction of the two electrodes disposed in the reference oxygen chamber is greater than a thickness of the entire insulative protection layer disposed in the reference oxygen chamber.

6. The gas sensor according to claim 1, wherein the another insulative protection layer is not formed on the other of the selected one of the two electrodes disposed in the reference oxygen chamber.

7. The gas sensor according to claim 1, wherein the another insulative protection layer is formed on the other of the selected one of the two electrodes disposed in the reference oxygen chamber.

8. The gas sensor according to claim 1, wherein a thickness of the gap is from 20 to 50 m.

9. The gas sensor according to claim 1, wherein a thickness of the gap is greater than a thickness of the insulative protection layer.

10. The gas sensor according to claim 8, wherein the thickness of the gap is greater than the thickness of the insulative protection layer.

* * * * *